United States Patent
Oura et al.

(10) Patent No.: US 12,419,611 B2
(45) Date of Patent: Sep. 23, 2025

(54) PATIENT MONITOR, PHYSIOLOGICAL INFORMATION MEASUREMENT SYSTEM, PROGRAM TO BE USED IN PATIENT MONITOR, AND NON-TRANSITORY COMPUTER READABLE MEDIUM IN WHICH PROGRAM TO BE USED IN PATIENT MONITOR IS STORED

(71) Applicant: NIHON KOHDEN CORPORATION, Tokyo (JP)

(72) Inventors: Mitsuhiro Oura, Tokyo (JP); Sou Kumagai, Tokyo (JP); Wataru Matsuzawa, Tokyo (JP); Naoki Kobayashi, Tokyo (JP); Hiroto Sano, Tokyo (JP); Takashi Mori, Tokyo (JP); Nobuyuki Yasumaru, Tokyo (JP); Kazuya Nagase, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 303 days.

(21) Appl. No.: 15/770,665

(22) PCT Filed: Oct. 5, 2016

(86) PCT No.: PCT/JP2016/079690
§ 371 (c)(1),
(2) Date: Apr. 24, 2018

(87) PCT Pub. No.: WO2017/081962
PCT Pub. Date: May 18, 2017

(65) Prior Publication Data
US 2018/0296188 A1 Oct. 18, 2018

(30) Foreign Application Priority Data
Nov. 13, 2015 (JP) ................................. 2015-223061

(51) Int. Cl.
*A61B 8/14* (2006.01)
*A61B 5/00* (2006.01)
(Continued)

(52) U.S. Cl.
CPC ................ *A61B 8/463* (2013.01); *A61B 5/00* (2013.01); *A61B 5/7445* (2013.01); *A61B 8/14* (2013.01);
(Continued)

(58) Field of Classification Search
CPC ......... A61B 8/463; A61B 5/7445; A61B 8/14; A61B 5/00; A61B 5/01; A61B 5/021;
(Continued)

(56) References Cited

U.S. PATENT DOCUMENTS 5,687,717 A * 11/1997 Halpern ............... A61B 5/0205
128/903
6,188,407 B1 * 2/2001 Smith .................... A61B 5/742
345/902
(Continued)

FOREIGN PATENT DOCUMENTS

CN 103544688 A 1/2014
CN 105050657 A 11/2015
(Continued)

OTHER PUBLICATIONS

International Search Report (PCT/ISA/210) dated Dec. 20, 2016 issued by the International Searching Authority in counterpart International Application No. PCT/JP2016/079690.
(Continued)

*Primary Examiner* — Cesar B Paula
*Assistant Examiner* — Zelalem Shalu
(74) *Attorney, Agent, or Firm* — Sughrue Mion, PLLC

(57) ABSTRACT

A patient monitor (10) acquires a vital sign that is based on a physiological signal of a subject, and an ultrasonic image
(Continued)

that is based on a reflected wave of an ultrasonic wave which is irradiated onto the subject. A display section (16) displays information of the subject. A control section (14) switches between a first mode in which a screen containing information of the vital sign is displayed on the display section (16), and a second mode in which a screen containing the ultrasonic image is displayed on the display section (16).

16 Claims, 8 Drawing Sheets

(51) Int. Cl.
  A61B 5/021    (2006.01)
  A61B 5/0245   (2006.01)
  A61B 8/00     (2006.01)
  G06F 3/0484   (2022.01)
  G16H 40/63    (2018.01)
  A61B 5/01     (2006.01)
  A61B 5/083    (2006.01)

(52) U.S. Cl.
  CPC .......... *G06F 3/0484* (2013.01); *G16H 40/63* (2018.01); *A61B 5/01* (2013.01); *A61B 5/021* (2013.01); *A61B 5/0245* (2013.01); *A61B 5/083* (2013.01)

(58) Field of Classification Search
  CPC ..... A61B 5/0245; A61B 5/083; G06F 3/0484; G16H 40/63
  See application file for complete search history.

(56) References Cited

U.S. PATENT DOCUMENTS

| | | | | |
|---|---|---|---|---|
| 8,137,273 | B2* | 3/2012 | Everett | A61B 5/022 600/500 |
| 8,317,714 | B2* | 11/2012 | Hendriks | A61B 8/463 600/443 |
| 2003/0045796 | A1 | 3/2003 | Friedman | |
| 2003/0163045 | A1* | 8/2003 | Gatzke | A61B 5/00 600/437 |
| 2004/0133115 | A1 | 7/2004 | Hamilton et al. | |
| 2006/0058660 | A1* | 3/2006 | Sandy | A61B 5/339 600/437 |
| 2007/0016029 | A1* | 1/2007 | Donaldson | A61B 8/565 600/437 |
| 2007/0185390 | A1 | 8/2007 | Perkins et al. | |
| 2008/0039744 | A1 | 2/2008 | Hamilton | |
| 2008/0077012 | A1 | 3/2008 | Gunji | |
| 2009/0292181 | A1* | 11/2009 | Donaldson | G06F 19/321 600/301 |
| 2010/0113905 | A1* | 5/2010 | Park | G01S 7/52073 600/324 |
| 2011/0010473 | A1* | 1/2011 | Szolyga | G06F 1/1601 710/36 |
| 2011/0157480 | A1* | 6/2011 | Curl | G16H 40/67 348/739 |
| 2012/0022355 | A1* | 1/2012 | Byrd | A61B 8/565 600/373 |
| 2012/0116218 | A1 | 5/2012 | Martin et al. | |
| 2012/0165677 | A1* | 6/2012 | Li | A61B 8/5261 600/459 |
| 2014/0015856 | A1 | 1/2014 | Xiao et al. | |
| 2016/0015368 | A1* | 1/2016 | Poland | A61B 8/4405 600/447 |
| 2016/0030758 | A1 | 2/2016 | Guiney et al. | |
| 2016/0048291 | A1* | 2/2016 | Boshoff | G06F 3/04842 715/834 |
| 2016/0081597 | A1* | 3/2016 | Bhavaraju | A61B 5/7275 600/365 |
| 2020/0335205 | A1* | 10/2020 | Nye | G06T 7/0012 |

FOREIGN PATENT DOCUMENTS

| | | |
|---|---|---|
| JP | 59-032444 A | 2/1984 |
| JP | 5-228153 A | 9/1993 |
| JP | 8-256996 A | 10/1996 |
| JP | 11-332865 A | 12/1999 |
| JP | 2006-505294 A | 2/2006 |
| JP | 2008-073282 A | 4/2008 |
| JP | 2008-167838 A | 7/2008 |
| JP | 2009-294800 A | 12/2009 |
| JP | 2015-097687 A | 5/2015 |
| WO | 2009/138902 A1 | 11/2009 |

OTHER PUBLICATIONS

Written Opinion (PCT/ISA/237) dated Dec. 20, 2016 issued by the International Searching Authority in counterpart International Application No. PCT/JP2016/079690.
Communication dated Apr. 23, 2019, issued by the European Patent Office in counterpart European Application No. 16863926.8.
Communication dated Jul. 4, 2019, issued by the European Patent Office in counterpart European Application No. 16863926.8.
Office Action issued Sep. 4, 2019, by the Japanese Patent Office in counterpart Japanese Patent Application No. 2018-138827.
Communication dated Jul. 29, 2021 issued by the State Intellectual Property Office of the P.R.China in application No. 201680062612.0.
Communication issued on Nov. 15, 2024 from the China National Intellectual Property Administration for Chinese Patent Application No. 202210218336.X.

* cited by examiner

FIG. 7

| KIND OF VITAL SIGN | PRIORITY |
|---|---|
| HEART RATE (MEASUREMENT VALUE) | 1 |
| ELECTROCARDIOGRAM (WAVEFORM) | 3 |
| BLOOD PRESSURE (WAVEFORM) | 3 |
| BLOOD PRESSURE (MEASUREMENT VALUE) | 1 |
| CVP (WAVEFORM) | 3 |
| CVP (MEASUREMENT VALUE) | 1 |
| SpO2 (WAVEFORM) | 3 |
| SpO2 (MEASUREMENT VALUE) | 1 |
| RESPIRATION (WAVEFORM) | 2 |
| RESPIRATION RATE (MEASUREMENT VALUE) | 1 |

PATIENT MONITOR, PHYSIOLOGICAL INFORMATION MEASUREMENT SYSTEM, PROGRAM TO BE USED IN PATIENT MONITOR, AND NON-TRANSITORY COMPUTER READABLE MEDIUM IN WHICH PROGRAM TO BE USED IN PATIENT MONITOR IS STORED

TECHNICAL FIELD

The present disclosure relates to a patient monitor, a physiological information measurement system including the patient monitor, a program to be used in the patient monitor, and a non-transitory computer readable medium in which the program to be used in the patient monitor is stored. Particularly, the patient monitor relates to a monitor which handles a vital sign and an ultrasonic image.

BACKGROUND ART

As information for knowing the condition of a subject, various vital signs (the blood pressure, the body temperature, the respiration, the heart rate, the arterial oxygen saturation, and the like) are widely employed. Moreover, an ultrasonic inspection apparatus is used for knowing the condition of the chest, abdomen, or the like of the subject.

In recent years, techniques for simultaneously performing measurement of vital signs and ultrasonic diagnosis have been proposed. For example, Patent Literature 1 discloses a system in which an ultrasonic transducer can be connected to a patient monitor (FIG. 1 of Patent Literature 1). The system can simultaneously process both an ultrasonic image acquired by the ultrasonic transducer, and a vital parameter (vital sign) of the subject.

CITATION LIST

Patent Literature

Patent Literature 1: WO/2009/138902

SUMMARY OF INVENTION

Technical Problem

In a patient monitor, information of various kinds of vital signs (for example, the blood pressure, the heart rate, the respiration rate, the body temperature, and the arterial oxygen saturation) are displayed on a screen. As described above, moreover, also a configuration where an ultrasonic image is displayed in addition to various kinds of vital signs has been proposed. According to the configuration, the amount of information which is displayed on a display screen of a patient monitor is largely increased. Therefore, it is important to display a necessary and not excessive amount of information on a screen. Although an ultrasonic image is useful for knowing the condition of the abdomen or chest of a subject, particularly, an ultrasonic image occupies a large area of a screen, and therefore the displaying manner requires an improvement.

Therefore, there is an object to provide a screen which has a configuration where an ultrasonic image and a vital sign can be simultaneously displayed, and which is suitable for the user.

Solution to Problem

A mode for attaining the object is a patient monitor which acquires a vital sign that is based on a physiological signal of a subject, and an ultrasonic wave that is based on a reflected wave of an ultrasonic wave which is irradiated onto the subject, the patient monitor including:

a display section which displays information of the subject; and a control section that switches between a first mode in which a screen containing information of the vital sign is displayed on the display section, and a second mode in which a screen containing the ultrasonic image is displayed on the display section.

The control section switches between the first mode in which information of a vital sign is displayed, and a second mode in which an ultrasonic image is displayed. Namely, the screen on which the information of the vital sign is displayed, and that on which the ultrasonic image is displayed are switchingly displayed on the display section. Referring to the both screens, the user can refer to both of the information of the vital sign and the ultrasonic image. The occurrence of the display switching can disperse information to a display screen of the first mode, and that of the second mode. This can avoid a situation where the amount of information that is displayed on one screen is excessively large.

Therefore, the invention can provide a screen which has a configuration where an ultrasonic image and a vital sign can be simultaneously displayed, and which is suitable for the user.

BRIEF DESCRIPTION OF DRAWINGS

FIG. 7 is a view showing an example of a layout change in Embodiment 3.

DESCRIPTION OF EMBODIMENTS

Embodiment 1

Figure 1:
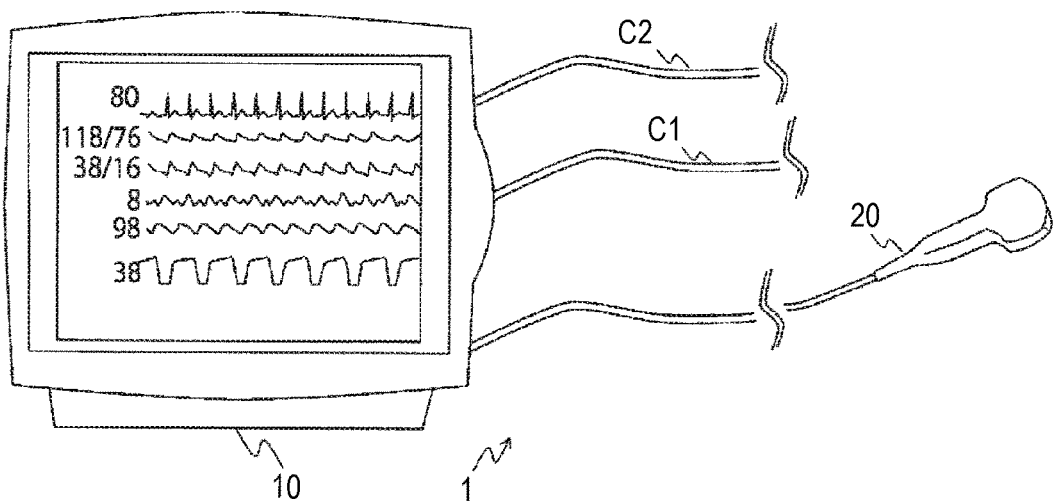
FIG. 1 is a view showing an example of the external configuration of a physiological information measurement system of Embodiment 1.

Hereafter, embodiment examples will be described with reference to the drawings. FIG. 1 is a conceptual view showing the external configuration of a physiological information measurement system 1 of the embodiment. The physiological information measurement system 1 has a patient monitor 10 and an ultrasonic measurement device 20. Although not illustrated, the patient monitor 10 is appropriately connected also to sensors (described later) through cable wires C1 and C2.

The patient monitor 10 measures various vital signs based on physiological signals which are acquired from various sensors 30 (described later with reference to FIG. 2) connected to a subject. The sensors 30 connected to the subject are various sensors used for measuring vital signs. For example, the sensors 30 include: a cuff used for measuring the blood pressure; electrodes (disposal electrodes; clip electrodes, and the like) used for measurement of an electrocardiogram, and the like; an SpO2 probe; a mask for measuring respiration; etc. The sensors 30 may be sensors which acquire physiological signals by using an invasive method. The vital signs which are the measurement targets are configured by, for example, the blood pressure, the body temperature, the respiration rate, the arterial oxygen saturation, an electrocardiogram, and the heart rate. The patient monitor 10 is a concept including a bedside monitor, a portable medical telemeter, a defibrillator having a function of measuring an electrocardiogram or the like, etc. Namely, the patient monitor 10 can be interpreted as various medical apparatuses which measure vital signs, and which display them. In the following description, the description will be made while it is assumed that the patient monitor 10 is a so-called bedside monitor.

The patient monitor 10 has connection ports (for example, connector jacks) which are to be connected to the various sensors 30. The ultrasonic measurement device 20 is a device which can be attached to and detached from the connection ports. When a probe 21 (described later) is contacted to the living body of the subject, the ultrasonic measurement device 20 acquires an ultrasonic image of the interior of the living body of the subject. The ultrasonic measurement device 20 is a device having a weight and size which allow the user (mainly, the doctor) to grasp the device, and a form in which a cable is connected to a probe head of a usual ultrasonic diagnosis apparatus.

The ultrasonic measurement device 20 is requested to be connectable to the patient monitor 10. Namely, the ultrasonic measurement device 20 may transmit and receive data to and from the patient monitor 10 through not only wired connection as illustrated, but also wireless connection.

Figure 2:
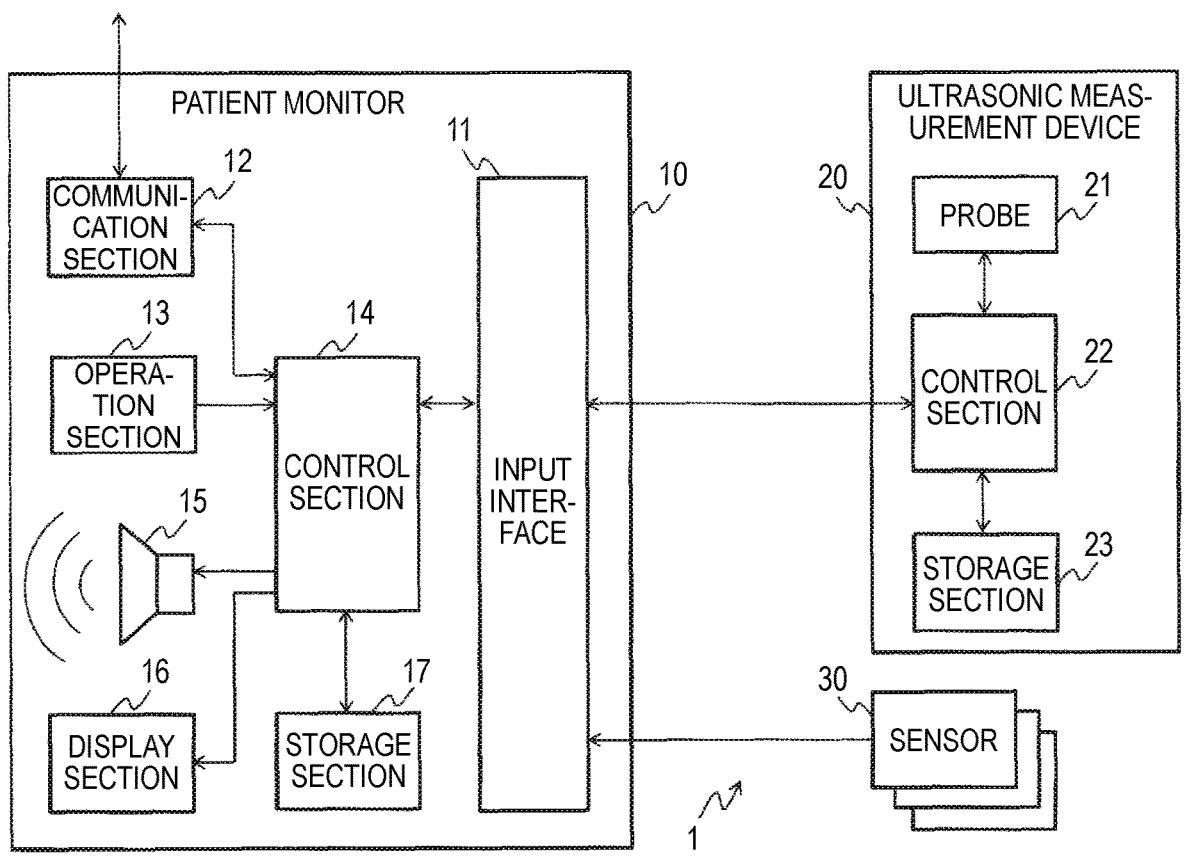
FIG. 2 is a block diagram showing the internal configuration of the physiological information measurement system of Embodiment 1.

Then, the electric configuration of the physiological information measurement system 1 will be described with reference to FIG. 2. FIG. 2 is a block diagram which is focused on the electric configuration of the physiological information measurement system 1. As described above, the sensors 30 are sensors for vital signs which are to be connected (for example, applied) to the living body of the subject.

The patient monitor 10 has an input interface 11, a communication section 12, an operation section 13, a control section 14, a speaker 15, a display section 16, and a storage section 17. Although not illustrated, the patient monitor 10 adequately includes an internal power supply and the like.

The input interface 11 is configured by the above-describe connection ports, their peripheral circuits, and the like. The input interface 11 supplies signals which are received from the sensors 30 and the ultrasonic measurement device 20, to the control section 14. The input interface 11 transmits a signal from the patient monitor 10 to the sensors 30 or the ultrasonic measurement device 20. As described later, the patient monitor 10 receives an ultrasonic image (or a reception signal based on which an ultrasonic image is produced) from the ultrasonic measurement device 20.

The communication section 12 transmits and receives data to and from other apparatuses (for example, a central monitor). For example, the communication section 12 is requested to satisfy a communication standard for a wireless LAN (Local Area Network) or the like. The communication section 12 may conduct a communication process through a wired cable.

The user (mainly, the doctor) performs an input operation on the patient monitor 10 through the operation section 13. The operation section 13 is configured by buttons, knobs, a rotary selector, keys, or the like which are disposed on, for example, the case of the patient monitor 10. An input through the operation section 13 is supplied to the control section 14.

The speaker 15 outputs various annunciation sounds such as an alarm. The speaker 15 performs annunciation in accordance with the control by the control section 14.

The display section 16 is configured by a display which is disposed on the case of the patient monitor 10, its peripheral circuits, and the like. The display section 16 displays various kinds of information of the subject. More specifically, the display section 16 displays information (waveforms and measurement values) of various vital signs, setting screens, and the like in accordance with the control by the control section 14 (see FIG. 1). Moreover, the display section 16 displays also an ultrasonic image in accordance with the control by the control section 14. The display control by the control section 14 will be described later with reference to FIG. 3A and the like.

A configuration (such as that similar to a so-called touch panel) in which the operation section 13 and the display section 16 are integrated with each other may be employed.

The storage section 17 stores various programs (including system software and various kinds of application software), and data (including measurement and set values of the blood pressure, the SpO2, and the like, an ultrasonic image which will be described later, and so on) which are to be used by the control section 14. The control section 14 adequately reads programs or data from the storage section 17. Moreover, the control section 14 appropriately writes data in the storage section 17. The storage section 17 is a secondary storage device which is disposed in the patient monitor 10, and configured by, for example, a hard disk drive which is disposed in the patient monitor 10. The storage section 17 is not limited to a device which is incorporated in the patient monitor 10, and may have a configuration where the section is attachable to and detachable from the patient monitor 10 (for example, a USB (Universal Serial Bus) memory which is attachable to and detachable from the patient monitor 10).

The control section 14 is a process section which performs various processes of the patient monitor 10. The control section 14 is configured by a CPU (Central Processing Unit) and its peripheral circuits, and realizes the operation by software or hardware. Specifically, the control section 14 performs acquisition of information (waveforms and measurement values of the blood pressure, the SpO2, the body temperature, and the like) of vital signs which are based on physiological signals acquired from the sensors 30, controls of alarm sounding which is based on the information of vital signs, and the like.

During monitoring of the subject, moreover, the control section 14 switches between a first mode in which a screen containing information of the vital signs is displayed on the display section 16, and a second mode in which a screen containing information of the ultrasonic image is displayed on the display section 16. The display switching will be described later in detail with reference to FIG. 3A and the like.

Then, the configuration of the ultrasonic measurement device 20 will be described. As shown in FIG. 1, the ultrasonic measurement device 20 is a device which is attachable to and detachable from the patient monitor 10. The ultrasonic measurement device 20 has a so-called probe-like shape. The ultrasonic measurement device 20 has a probe 21, a control section 22, and a storage section 23.

The ultrasonic measurement device 20 may be a device which operates with a power supply from the patient monitor 10, or have a configuration where an internal power supply is provided.

The probe 21 is contacted with (or adjoined to) the living body of the subject, and irradiates the living body with an ultrasonic wave. Moreover, the probe 21 receives a reflected ultrasonic wave (reflected wave). The probe 21 supplies the received ultrasonic wave to the control section 22.

The kind of the probe 21 is not particularly limited. Namely, the probe 21 may be of one of the convex type, the sector type, the linear type, and other types. An operation interface (knobs, buttons, an operation wheel, or the like) may be disposed on a case of the probe 21. The user operates the operation interface to change the setting and the like of the probe 21.

The control section 22 performs various settings of the probe 21, incorporation of the received signal acquired by the probe 21, and the like. For example, the control section 22 performs the following processes:

setting of the ultrasonic wave frequency of the probe 21
setting of the beam forming of the probe 21
calculation (matching and addition of reflection echo signals) of the reflected wave which is received by the probe 21, and formation of an ultrasonic reception beam
mode signal processing, CF signal processing, and Doppler signal processing on the ultrasonic reception beam
formation of an ultrasonic image by scan processing
calculation of measurement values of the blood flow volume, the respiration rate, the heart sound, the fetal movement, and the like based on the ultrasonic reception beam (or the ultrasonic image)
process of switching the ultrasonic mode (the B-mode, the M-mode, the D-mode, and the like)
detection of an error of the probe 21
transmission and reception of data to and from the patient monitor 10 (including also transmission of the ultrasonic image)

The control section 22 transfers the ultrasonic image which is produced by the above processes, to the patient monitor 10. Alternatively, the control section 22 may transfer a signal of the reflected wave acquired by the probe 21, as it is to the patient monitor 10. In the alternative, the control section 14 performs a process of producing an ultrasonic image based on the signal of the reflected wave.

The storage section 23 stores various programs (including system software and various kinds of application software), and data (including history and set values of the ultrasonic image, and the like) which are to be used by the control section 22. The control section 22 adequately reads programs or data from the storage section 23. Moreover, the control section 22 appropriately writes data in the storage section 23. The storage section 23 is a secondary storage device which is disposed in the ultrasonic measurement device 20, and configured by, for example, a hard disk drive which is disposed in the ultrasonic measurement device 20. The storage section 23 is not limited to a device which is incorporated in the ultrasonic measurement device 20, and may have a configuration where the section is attachable to and detachable from the ultrasonic measurement device 20 (for example, a USB (Universal Serial Bus) memory which is attachable to and detachable from the ultrasonic measurement device 20).

Then, the display control of the patient monitor 10 will be described in detail. The control section 14 controls the display of information of vital signs and an ultrasonic image. Specifically, the control section 14 switches between a first mode in which a screen containing information of the vital sign is displayed on the display section 16, and a second mode in which a screen containing information of the ultrasonic image is displayed on the display section 16.

The control section 14 may operate in another mode (a third mode, a fourth mode, or the like) in accordance with an operation performed on the operation section 13. For example, the control section 14 may be transferred to an operation mode in which various setting screens are displayed in accordance with a depression of the setting button.

The screen of the first mode is a screen for displaying information of vital signs (measurement values and waveforms of the blood pressure, the SpO2, the respiration, the body temperature, and the like). In addition to information of vital signs, various setting buttons and the like may be displayed on the screen of the first mode. The screen of the second mode is different from that of the first mode, and displays at least an ultrasonic image.

Figure 3A:
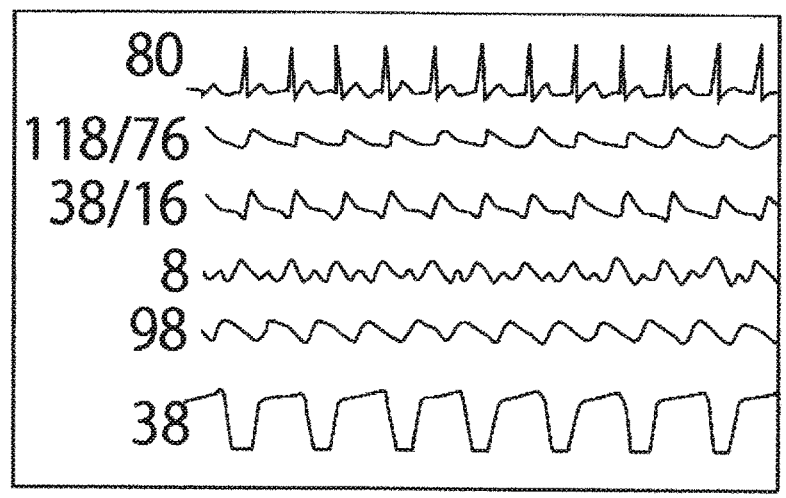
FIG. 3A is a view showing an example of a screen of a first mode and a screen of a second mode in Embodiment 1.

Hereinafter, examples of the screen of the first mode and that of the second mode will be described with reference to FIGS. 3A to 3C. FIG. 3A is a view showing an example of the screen of the first mode. Measurement values and waveforms of various vital signs (the blood pressure, the SpO2, the respiration, the body temperature, and the like) are displayed on the screen shown in the figure.

Figure 3B:
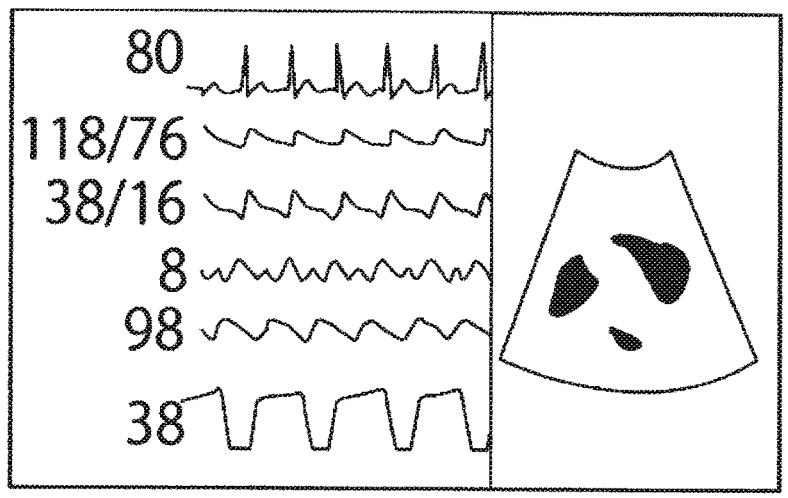
FIG. 3B is a view showing an example of the screen of the first mode and the screen of the second mode in Embodiment 1.
Figure 3C:
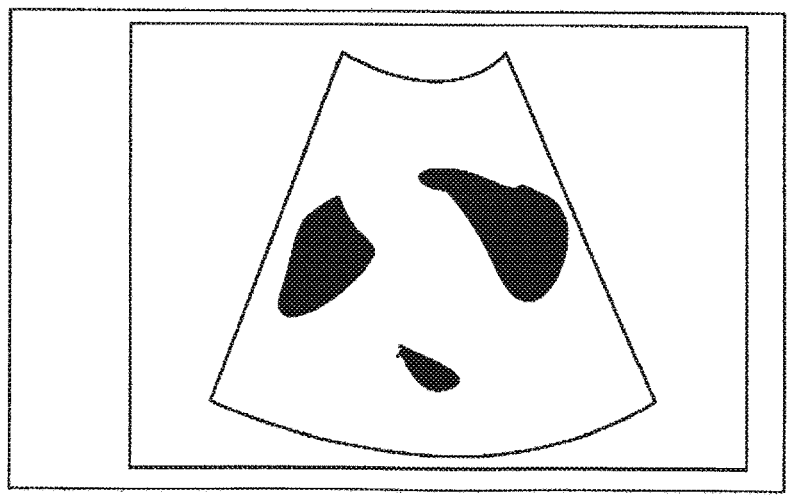
FIG. 3C is a view showing an example of the screen of the first mode and the screen of the second mode in Embodiment 1.

FIG. 3B is a view showing an example of the screen of the second mode. In addition to measurement values and waveforms of vital signs, an ultrasonic image acquired by the operation of the ultrasonic measurement device 20 is displayed on the screen shown in the figure. FIG. 3C is a view showing another example of the screen of the second mode. Only an ultrasonic image acquired by the operation of the ultrasonic measurement device 20 is displayed on the screen shown in the figure. The setting buttons and the like may be adequately displayed on the screen of the second mode shown in FIG. 3B or 3C. Namely, the screen of the second mode contains an ultrasonic image, and is different from the screen of the first mode. It is preferable that information (measurement values and waveforms) of vital signs can be always referred. Therefore, it is desirable that the default display screen of the second manner is the display mode such as shown in FIG. 3B.

The display of FIG. 3B is a mere example, and an ultrasonic image may be placed in a so-called side cabinet.

The size of a window in which an ultrasonic image is displayed may be changed by mouse cursor processing or the like.

In the case where a predetermined event (for example, (A) or (B) which will be described later) occurs, or predetermined conditions (for example, (C) or (D) which will be described later) are satisfied, the control section 14 switches the operation modes (the first mode and the second mode) in which the respective display targets are different from each other. Hereinafter, the mode switching will be described in detail.

Examples of the timing when the control section 14 switches between the first mode and the second mode are as follows:
  (A) a case where an input for mode switching is entered through the operation interface
  (B) a case where attachment or detachment between the ultrasonic measurement device 20 and the patient monitor 10 occurs
  (C) a case where a change state of the ultrasonic image (or the signal of the reflected wave) from the ultrasonic measurement device 20 becomes a predetermined state
  (D) a case where a vital sign enters a predetermined degraded state (an alarming state, degraded for a long term, or the like), or recovers from the degraded state
Hereinafter, (A) to (D) above will be described.
  (A) The case where an input for mode switching is entered through the operation interface When the user operates various operation interfaces (for example, buttons, knobs, a dial type input section, and the like) disposed on the case of the ultrasonic measurement device 20 to instruct the mode switching, the ultrasonic measurement device 20 transmits a switch signal. Upon reception of the switch signal from the ultrasonic measurement device 20, the control section 14 performs the mode switching. In the case where the switch signal is received during the operation in the first mode, specifically, the control section 14 switches to the second mode. In the case where the switch signal is received during the operation in the second mode, similarly, the control section 14 switches to the first mode.

When the mode switching is instructed by an operation on the operation section 13 of the patient monitor 10, the control section 14 performs the mode switching process. As described above, the operation section 13 may be a touch panel or the like which is disposed on the display screen of the patient monitor 10, or button, knobs, switches, or the like which are disposed on the case of the patient monitor 10. In the case where instructions for switching are issued during the operation in the first mode, the control section 14 switches to the second mode. In the case where the switch signal is received during the operation in the second mode, similarly, the control section 14 switches to the first mode.

The operation interface which is used for switching the mode may be a device which can be attached to and detached from the ultrasonic measurement device 20 or the patient monitor 10. The operation interface may be disposed between a probe head of the ultrasonic measurement device 20 and the connector jack.

(B) The case where attachment or detachment between the ultrasonic measurement device 20 and the patient monitor 10 occurs In the case where the ultrasonic measurement device 20 is connected to the patient monitor 10 (for example, inserted into the connector jack of the patient monitor 10), the control section 14 switches from the first mode to the second mode. In the case where the ultrasonic measurement device 20 is connected, namely, the control section 14 switches to the operation mode (second mode) in which an ultrasonic image is displayed.

In the case where the connection between the ultrasonic measurement device 20 and the patient monitor 10 is ended (for example, extracted from the connector jack of the patient monitor 10), by contrast, the control section 14 switches from the second mode to the first mode. In the case where the ultrasonic measurement device 20 is extracted, namely, the control section 14 switches to the first mode in which vital signs are mainly displayed.

The insertion/extraction of the ultrasonic measurement device 20 may be sensed by using a usual technique (for example, a voltage change of a connector pin) or the like.
  (C) The case where a change state of the ultrasonic image or the signal of the reflected wave from the ultrasonic measurement device 20 becomes a predetermined state As described above, the ultrasonic measurement device 20 transmits the ultrasonic image or the signal of the reflected wave to the patient monitor 10. In the following description, it is assumed that the ultrasonic measurement device 20 transmits the signal of the reflected wave (hereinafter, referred to as the reflection wave signal).

In the case where the signal of the reflection wave signal is largely changed (the change rate of pixels exceeds a predetermined threshold), for example, it is considered that the reflection wave signal indicates a signal which is reflected from the interior of the living body of the subject. When the change is detected, therefore, the control section 14 switches from the first mode to the second mode. Namely, the control section 14 switches to the operation mode (second mode) in which an ultrasonic image is displayed.

In the case where the reflection wave signal is not changed for a constant period of time or longer (the change amount of the reflection wave signal does not exceed a predetermined threshold), by contrast, it is supposed that the reflection wave signal does not indicate a signal which is reflected from the interior of the living body of the subject. In the case where the reflection wave signal is not changed for the constant period of time or longer, therefore, the control section 14 switches to the first mode in which vital signs are mainly displayed.

The analysis of the reflection wave signal is not limited to the above-described comparisons with the thresholds, and may be performed by using the change rate of the signal or the like. Although, in the above description, it is assumed that the reflection wave signal is transmitted from the ultrasonic measurement device 20, the control section 14 can similarly perform the process even in the case where an ultrasonic image is transmitted from the ultrasonic measurement device 20. For example, the control section 14 may detect a temporal pixel change of an ultrasonic image, and perform the mode switching based on the pixel change.
  (D) The case where a vital sign enters a predetermined degraded state (an alarming state, degraded for a long term, or the like), or recovers from the degraded state As described above, the patient monitor 10 acquires various vital signs through the sensors 30. In the case where the measurement value of a vital sign enters a predetermined degraded state, the control section 14 performs the mode switching. The predetermined degraded state includes, in addition to a case where one of the vital signs has an abnormal value, that where a certain vital sign is degraded for a long term (for example, the respiration rate is reduced for 5 minutes or longer), that where a plurality of vital signs have a value similar to an abnormal value, and the like.

In the case where the measurement value of a certain vital sign enters an alarming state during the operation of the second mode, for example, the control section 14 switches to the first mode, and performs an alarm sounding control and the like. In the case where, after performing the switching, a predetermined period of time has elapsed from the timing when the measurement value of the vital sign becomes a value, by contrast, the control section 14 switches from the first mode to the second mode.

An example of the mode switching process performed by the control section 14 has been described. (A) to (D) which have been described above are mere examples, and the mode switching may be performed by using an event other than the above-described events as a trigger. Moreover, the user may set the timing when the mode switching is performed, through a setting screen (not shown). For example, the user can make only (A) above valid (only the manual switching by the user is made valid). The user may define other events or conditions under which the mode switching occurs (in other words, events or conditions other than (A) to (D) above may be defined).

Furthermore, the user may be enabled to define setting in which switching between the first mode and the second mode is inhibited. For example, the user may perform the setting through the operation section 13 of the patient monitor 10. In the case where the setting in which switching between the first mode and the second mode is inhibited is made, the control section 14 performs a control so as not to perform mode switching between the first mode and the second mode. In the case where the setting of inhibition of the mode switching is performed, the user can continue to see the screen which is currently referred. In the case where, although the user recognizes degradation of the vital sign, the user wishes to check the cause of the degradation of the disease condition through an ultrasonic image, for example, the user can continue to refer the second mode in which an ultrasonic image is displayed.

Even in the case where the mode switching is inhibited, and the display in the second mode is continued, the control section 14 may perform as usual the alarm sounding control through the speaker 15. This enables the user to continue to refer the ultrasonic image while knowing an abnormality of the subject because of the alarm sounding.

Then, effects of the physiological information measurement system 1 of the embodiment will be described. In the case where the patient monitor 10 has a configuration where an ultrasonic image is handled, it is often that the ultrasonic image is temporarily referred in order to know the disease condition of the subject. On the other hand, the user usually wishes to always refer information of vital signs (for example, measurement values and waveforms of the blood pressure, the SpO2, the body temperature, and the respiration rate). As described above, an ultrasonic image and information of vital signs have different properties, and therefore it is important to display them while adequately switching the screens.

In the above-described configuration, the control section 14 switches between the first mode in which information of vital signs is displayed, and the second mode in which an ultrasonic image is displayed. Namely, the screen on which the information of the vital signs is displayed, and that on which the ultrasonic image is displayed are switchingly displayed on the display section 16. When referring the two screens, the user can refer both the information of the vital sign, and the ultrasonic image. Since the display switching occurs, information can be dispersed to the display screen in the first mode, and that in the second mode. This can avoid a situation where the amount of information that is displayed on one screen is excessively large.

When one of (A) to (D) above occurs, for example, the mode switching by the control section 14 is performed. Since the mode is switched in the case where a predetermined event occurs, or predetermined conditions are satisfied (namely, one of (A) to (D) above occurs), the user can refer information of vital signs and an ultrasonic image at appropriate timings. In the case where the mode switching is performed in accordance with an operation conducted on the operation interface ((A) above), for example, the user can switch the display at a desired timing. This enables the user to immediately access necessary information.

Moreover, the control section 14 may perform the mode switching in accordance with the attachment/detachment state of the ultrasonic measurement device 20 ((B) above). This enables the user to refer an ultrasonic image immediately after a state where the ultrasonic image can be referred is attained. Alternatively, the user can refer only information of vital signs immediately after an ultrasonic image cannot be acquired.

The control section 14 may switch the mode in accordance with the reception signal (or an ultrasonic image) from the ultrasonic measurement device 20 ((C) above). This enables the user to refer an ultrasonic image only in the case where a useful ultrasonic image can be acquired. Namely, the user can refer an ultrasonic image only in the case where it is useful to refer the ultrasonic image.

The control section 14 may switch the mode in accordance with the state of the measurement value of a vital sign ((D) above). This causes information of a vital sign to be preferentially displayed in the case where the measurement value of the vital sign is abnormal (possibly becomes abnormal). Therefore, the user can correctly know degradation of the vital sign.

Embodiment 2

The patient monitor 10 of the embodiment is characterized in that a part of setting changing processes is inhibited in accordance with the current operation mode. Hereinafter, points of the physiological information measurement system 1 of the embodiment which are different from Embodiment 1 will be described. In the following description, the processing sections which are indicated by names and reference numerals that are similar to those used in Embodiment 1 perform processes similar to those of Embodiment 1 unless particularly described (the same shall apply to Embodiment 3).

The configuration of the physiological information measurement system 1 is similar to FIG. 1. The control section 14 in the embodiment prohibits (inhibits) setting which has been performed through the operation section 13 or the like, in accordance with the current operation mode (the first mode or the second mode). Hereinafter, a detailed example will be described.

In the case where the first mode is set, the control section 14 inhibits setting related to acquisition of an ultrasonic image. For example, the setting is change setting of an ultrasonic diagnosis mode (B-mode, M-mode, and D-mode), or the like.

In the case where the second mode is set, the control section 14 inhibits setting related to acquisition and display of a vital sign. The setting is related to measurements of various vital signs (the blood pressure, the respiration, the body temperature, and the SpO2), and for example setting related to the maximum pressurization value during a non-invasive blood pressure measurement, and the like.

Figure 4:
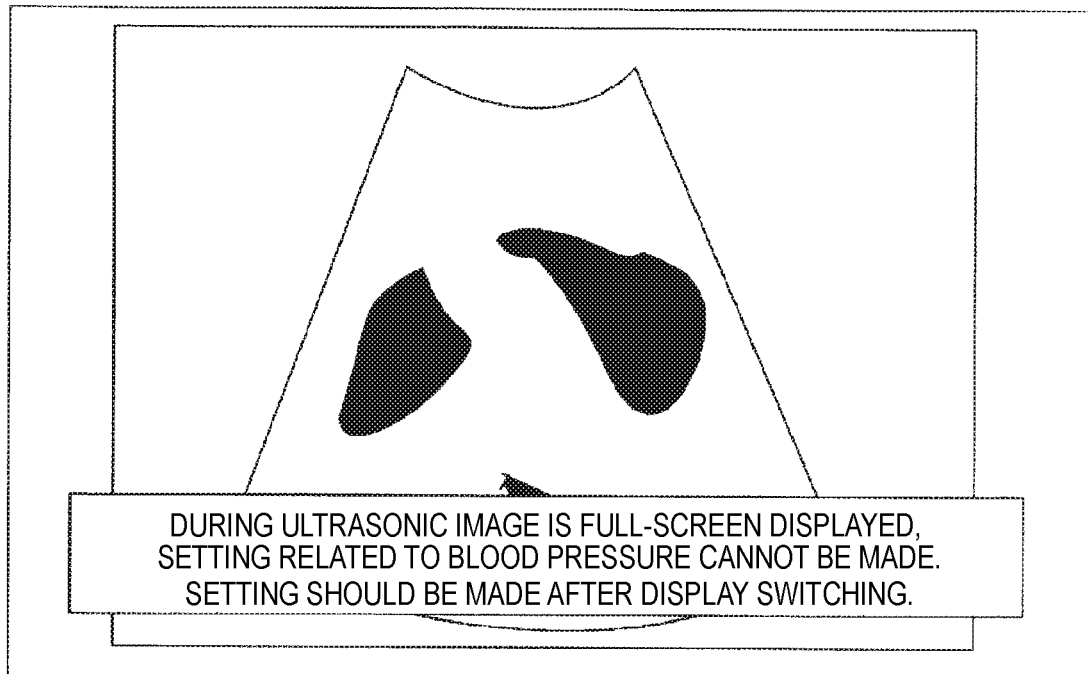
FIG. 4 is a view showing an example of a display screen in Embodiment 2.

As shown in FIG. 4, in the case where a prohibited setting operation is performed (in the case where a setting operation related to an ultrasonic wave is performed during the first mode, or that related to a vital sign is performed during the second mode), the control section 14 may cause a message indicating that the setting cannot be performed, to be displayed. When referring to the message, the user can know that the prohibited operation is being performed.

Then, effects of the patient monitor 10 of the embodiment will be described. In the case where the first mode is set, as described above, setting related to acquisition of an ultrasonic image is inhibited. It is considered that, in the case where the first mode is set, the user wishes to refer to the vital signs of the subject. In other words, it is considered that, in the case where the first mode is set, an ultrasonic wave is unconsidered in most situations. In this case, when setting related to an ultrasonic wave is inhibited, it is possible to avoid a situation where, when the mode is switched to the second mode, the patient monitor 10 operates under an unintended setting state.

In the case where the second mode is set, similarly, setting related to measurement of a vital sign is inhibited. It is considered that, in the case where the second mode is set, the user wishes to refer to an ultrasonic image related to the subject. In other words, it is considered that, in the case where the second mode is set, the attention is directed toward acquisition of an ultrasonic image rather than a vital sign. In this case, when setting related to a vital sign is inhibited, it is possible to avoid a situation where the process of measuring the vital sign operates under unintended set contents.

Embodiment 3

The patient monitor 10 of the embodiment is characterized in that the layout of a screen on which both an ultrasonic image and information of vital signs are displayed is changed under predetermined conditions. Hereinafter, points of the physiological information measurement system 1 of the embodiment which are different from Embodiment 1 will be described.

The configuration of the physiological information measurement system 1 of the embodiment is approximately identical with Embodiment 1 (FIG. 2). However, the display control by the control section 14 is different. The display control will be described in detail.

Figure 5:
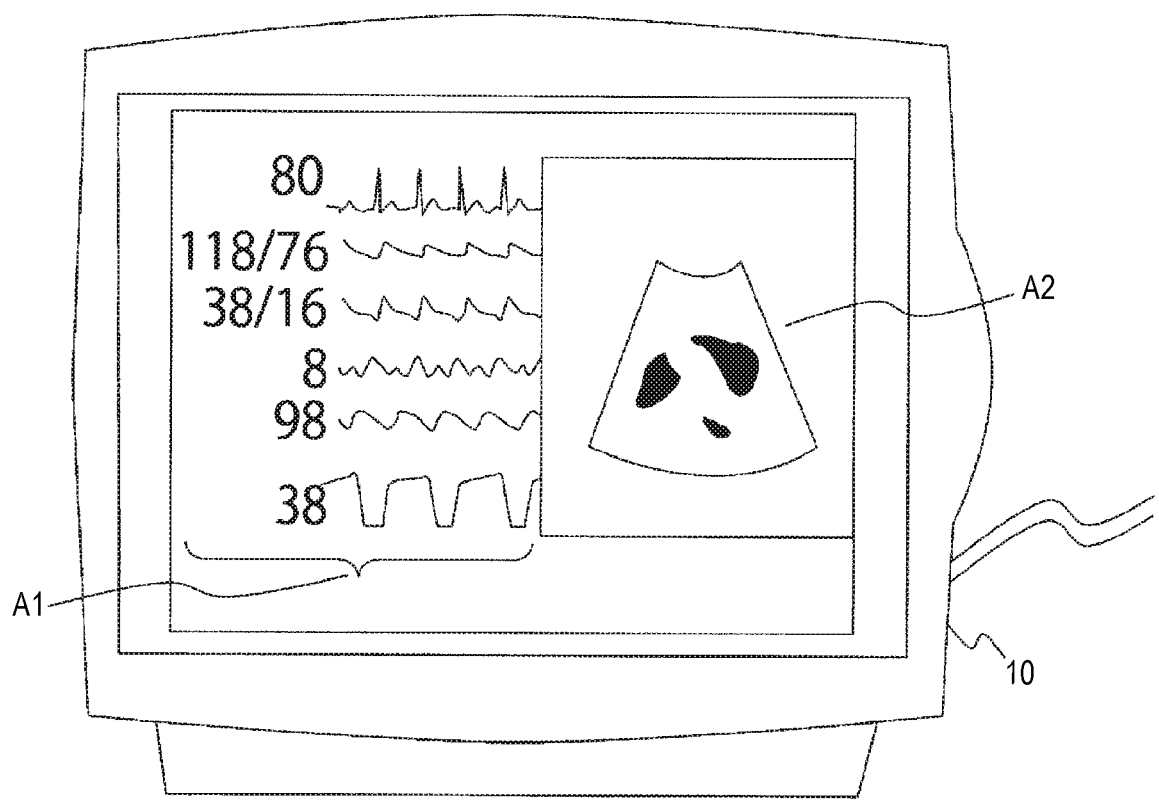
FIG. 5 is a view showing an example of a display screen in Embodiment 3.

In the case where the ultrasonic measurement device 20 is connected to the patient monitor 10, the control section 14 causes a screen on which an ultrasonic image and information (waveforms and measurement values) of vital signs are displayed, to be displayed on the display section 16. FIG. 5 shows an example of the screen. As illustrated, a region A1 where various vital signs are displayed, and a region A2 where an ultrasonic image is displayed are displayed.

In the case where the ultrasonic measurement device 20 is not connected to the patient monitor 10, of course, the control section 14 can cause only the region A1 where information of vital signs is displayed, to be displayed. Namely, the display section 16 displays at least one of information of vital signs and an ultrasonic image.

In the embodiment, the control section 14 is not always required to perform the mode switching (the first mode and the second mode). In the embodiment, the control section 14 changes the layout of the displayed screen in the case where a predetermined event occurs. Predetermined events functioning as a trigger for a layout change are as follows:

(E) a case where the size or position of the display region for an ultrasonic image is changed (F) a case where the measurement value of a certain vital sign becomes abnormal (a vital sign enters a predetermined degraded state)

Hereinafter, (E) and (F) above will be described.

(E) The case where the size or position of the display region for an ultrasonic image is changed Here, the size change includes a case where the display manner is changed from the non-display of an ultrasonic image (i.e., the vertical size=0 and the lateral size=0) to the display (the vertical size>0 and the lateral size>0). The change of the position indicates a change of the display position (coordinates) of an ultrasonic image. In the case where the size of the display region for an ultrasonic image is changed, this means a change of the display region for information of vital signs. Therefore, the control section 14 changes the layout in accordance with the display size and position of an ultrasonic image. The layout change may be performed in accordance with, for example, the following change rules.

Figure 6A:
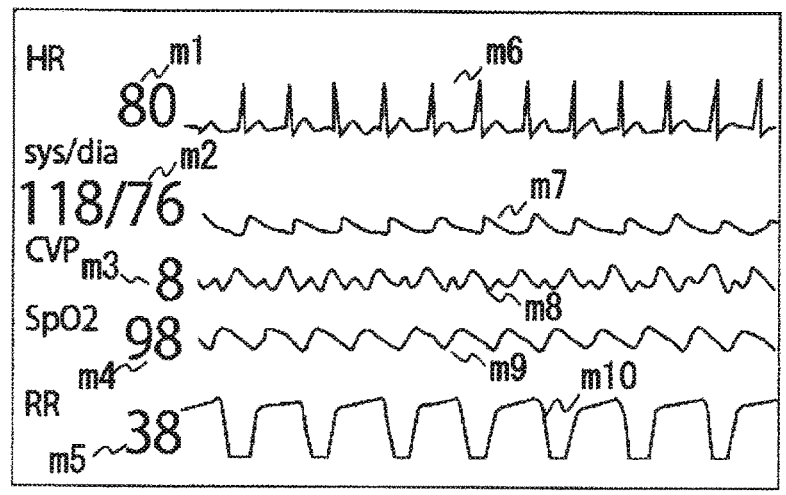
FIG. 6A is a view showing an example of a layout change in Embodiment 3.

Rule 1: the layout is changed so that measurement values (numerical values) of various vital signs are preferentially displayed as compared with measurement waveforms Rule 2: the layout is changed in accordance with a preset priority order Rule 3: the layout is changed so that a vital sign which is in a predetermined abnormal state (for example, the vital sign becomes a state where an alarm is to be sounded) is preferentially displayed Hereinafter, Rules 1 to 3 above will be described. Firstly, Rule 1 will be described with reference to FIGS. 6A to 6C. FIG. 6A is a view showing a display screen before the ultrasonic measurement device 20 is connected. Measurement values m1 to m5 and measurement waveforms m6 to m10 of various vital signs (the heart rate (HR), the blood pressures (sys/dia), the CVP, the SpO2, and the respiration rate (RR)) are displayed on the display screen. The control section 14 may produce the display screen by performing a display control which is usually conducted in the patient monitor 10.

Figure 6B:
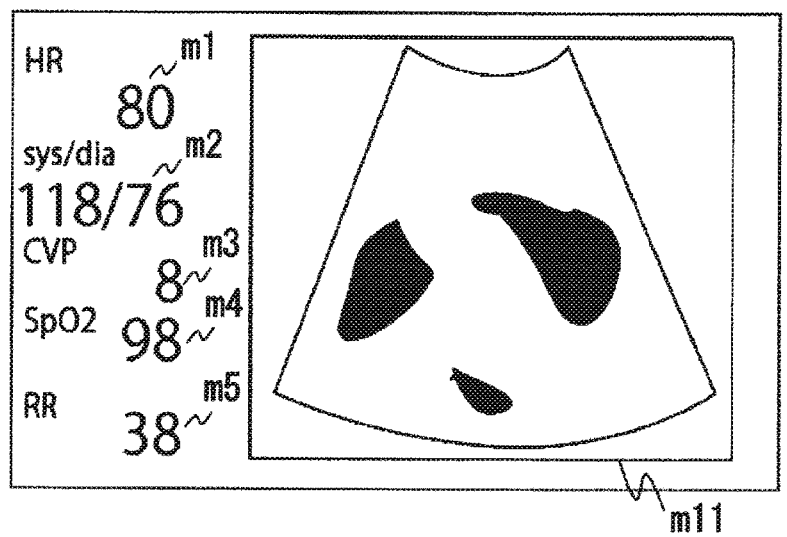
FIG. 6B is a view showing an example of a layout change in Embodiment 3.

It is assumed that, in the display state of FIG. 6A, instructions for changing the display size of an ultrasonic image (for example, connection of the ultrasonic measurement device 20) are issued. In accordance with the instructions, the control section 14 changes the layout so that an ultrasonic image is displayed, and only the measurement values of the various vital signs are displayed. FIG. 6B shows an example of the display screen after the change of the layout. On the display screen, as illustrated, an ultrasonic image m11 is displayed in addition to the measurement values (m1 to m5) of the various vital signs.

Figure 6C:
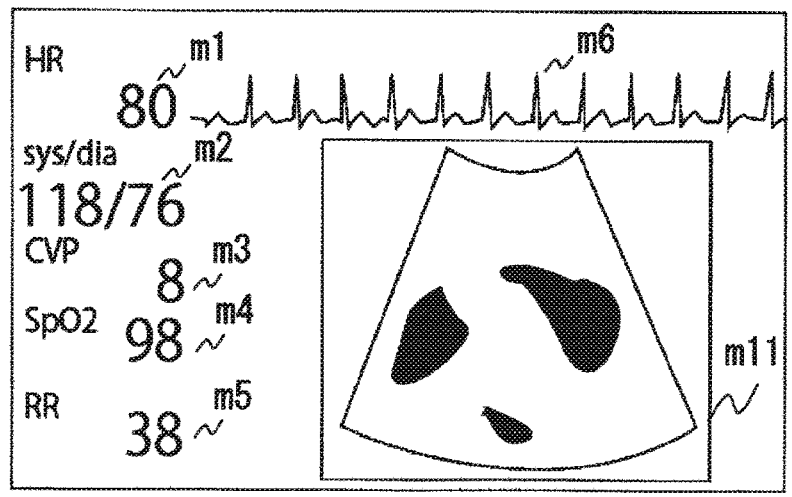
FIG. 6C is a view showing an example of a layout change in Embodiment 3.

Depending on the size of the ultrasonic image m11, the control section 14 may cause also a further measurement wave(s) to be displayed as far as possible. FIG. 6C shows an example in which also an electrocardiogram waveform m6 is displayed in addition to the display manner of FIG. 6B. In this way, the control section 14 may change the layout so that information the amount of which is large as far as possible can be displayed depending on the size of the ultrasonic image m11. The size of the ultrasonic image m11 may be previously determined by default, or may be adequately changed by, for example, operating a mouse.

Then, Rule 2 above will be described. The user previously defines each of the vital signs whether the vital sign is preferentially displayed or not. FIG. 7 shows an example of the definition of preferential display. In the example, measurement values are assigned a high priority (Priority=1), and a respiration waveform is assigned a next high priority (Priority=2). The priorities may be set by default. Alternatively, priorities may not be assigned to all of the vital signs, and vital signs to which high priorities are to be assigned may be defined.

Figure 8A:
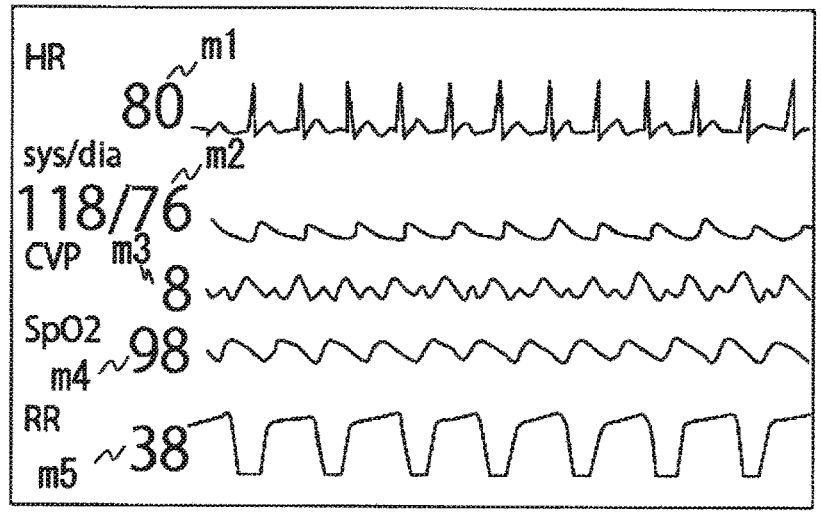
FIG. 8A is a view showing an example of a layout change in Embodiment 3.

The control section 14 changes the layout based on the priorities and the size of the ultrasonic image. FIG. 8A is a view showing a display screen before the ultrasonic measurement device 20 is connected. The measurement values m1 to m5 and measurement waveforms m6 to m10 of various vital signs are displayed on the display screen.

Figure 8B:
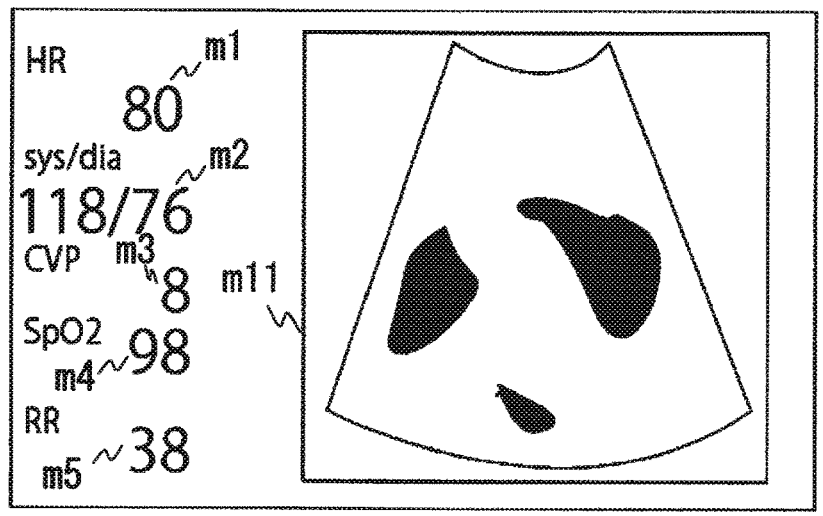
FIG. 8B is a view showing an example of a layout change in Embodiment 3.

It is assumed that, in the display state of FIG. 8A, instructions for changing the display size of the ultrasonic image m11 (for example, connection of the ultrasonic measurement device 20) are issued. The control section 14 acquires the size (for example, the default size) of the ultrasonic image, and, based on the size, calculates the size of the display region for the vital signs. Then, the control section 14 produces a layout in which information is sequentially inserted into the display region size in the order of higher priorities. FIG. 8B shows a layout example which is produced based on the priorities of FIG. 7. In the layout example, information having the high priority (Priority=1) is displayed.

Figure 8C:
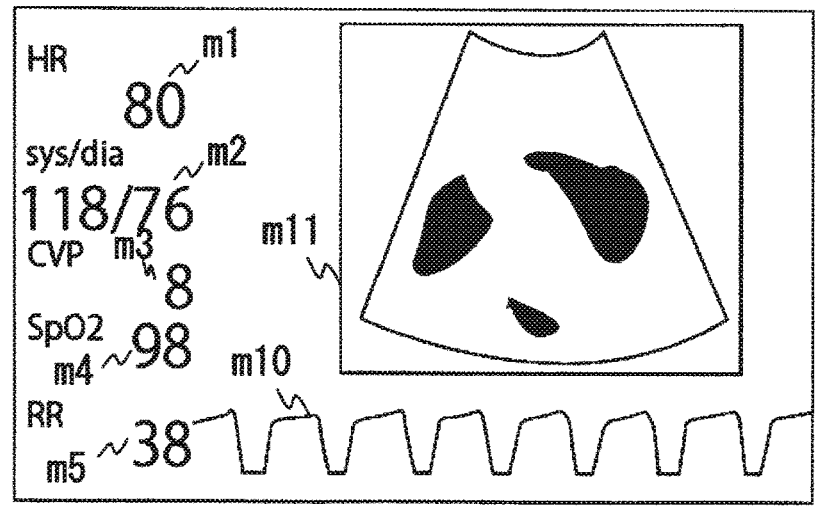
FIG. 8C is a view showing an example of a layout change in Embodiment 3.

FIG. 8C is a view showing a layout example in which the display size of the ultrasonic image m11 is smaller than that in FIG. 8B. In the layout example, also the respiration waveform m10 having the next high priority (Priority=2) is displayed in addition to the information having the high priority (Priority=1).

Figure 9A:
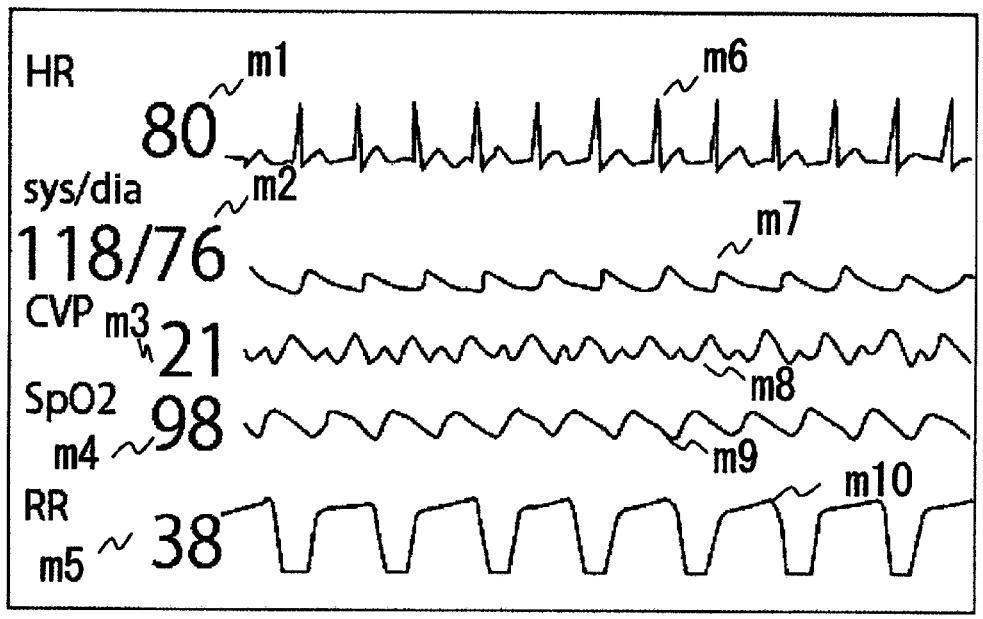
FIG. 9A is a view showing an example of a layout change in Embodiment 3.

Then, Rule 3 above will be described. The control section 14 causes the measurement value and waveform of a vital sign in a predetermined abnormal state (for example, a state where an alarm is to be sounded) to be preferentially displayed. FIG. 9A is a view showing a display screen before the ultrasonic measurement device 20 is connected. The measurement values m1 to m5 and measurement waveforms m6 to m10 of various vital signs are displayed on the display screen.

Figure 9B:
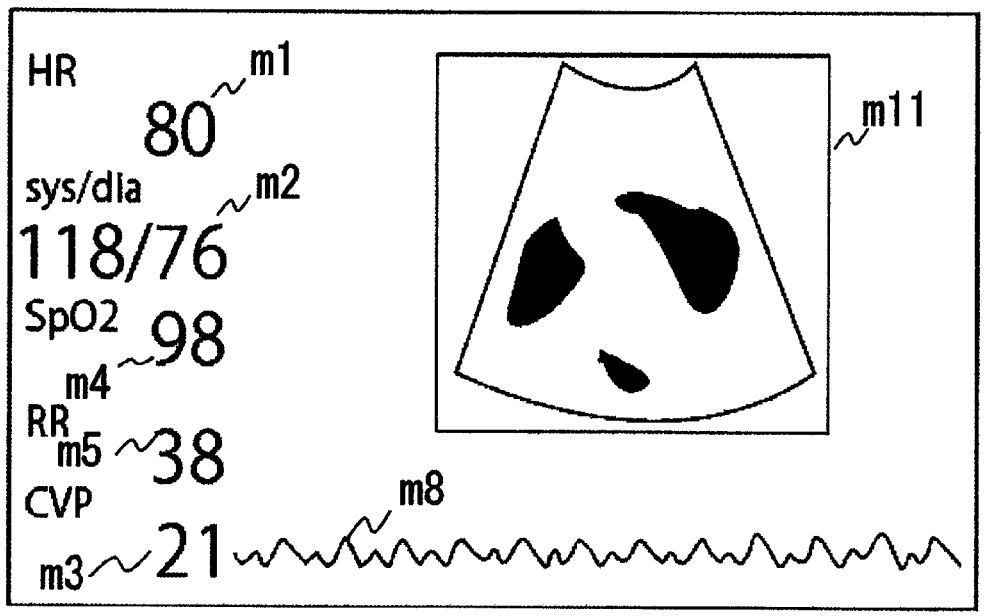
FIG. 9B is a view showing an example of a layout change in Embodiment 3.

It is assumed that, in the display state of FIG. 9A, instructions for changing the display size of the ultrasonic image m11 (for example, connection of the ultrasonic measurement device 20) are issued. The control section 14 acquires the size (for example, the default size) of the ultrasonic image, and, based on the size, calculates the size of the display region for the vital signs. The control section 14 causes the vital sign in the alarming state to be preferentially displayed in the display region for the vital signs, and then measurement values and the like in the respective normal value regions to be sequentially displayed. Since, in FIG. 9B, the CVP (Central Venous Pressure) has an abnormal value (21 mmHg with respect to the normal range of 10 mmHg or less), also the measurement waveform m8 is displayed in addition to the measurement value m3 of the CVP. In the case where the display position of the ultrasonic image is changed, the control section 14 may perform a control so as to move the measurement value and waveform of the vital sign in an abnormal state to a position which can be easily viewed (for example, the vicinity of the center of the display).

(F) The case where the measurement value of a certain vital sign becomes abnormal (a vital sign enters a predetermined degraded state)

Then, an example of a second event functioning as a trigger for the above-described layout change will be described. During an ultrasonic image is displayed, the control section 14 adequately determines whether the measurement value of each of vital signs is an abnormal value or not. If a vital sign having an abnormal value is detected, the control section 14 changes the layout so that detailed information of the vital sign is displayed.

Figure 10A:
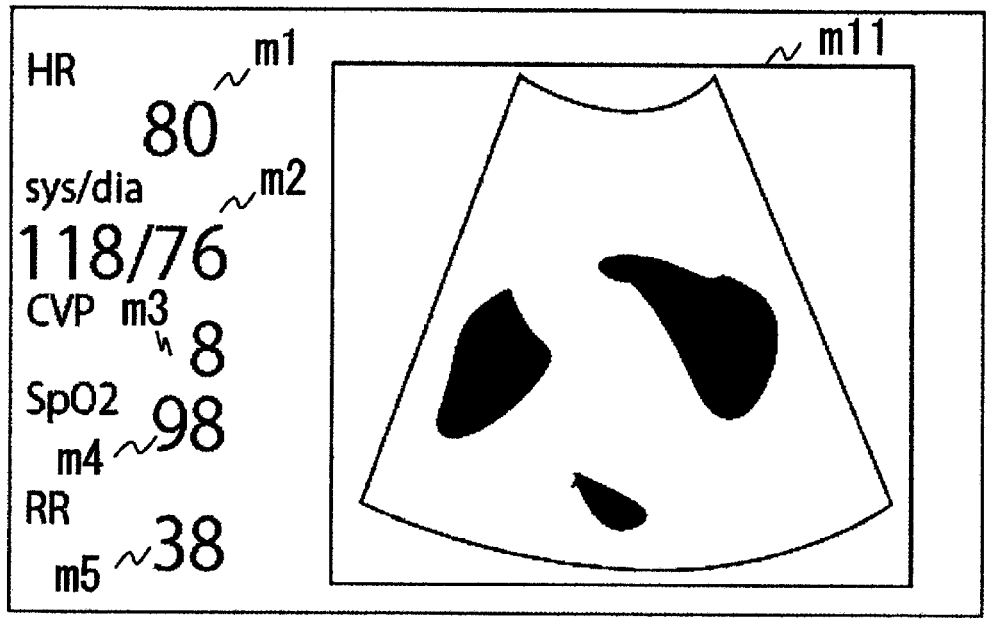
FIG. 10A is a view showing an example of a layout change in Embodiment 3.

Hereinafter, a specific example will be described with reference to FIGS. 10A and 10B. FIG. 10A shows a display screen in the case where the measurement values of the vital signs are normal. The measurement values m1 to m5 of the vital signs, and the ultrasonic image m11 are displayed on the display screen. Here, it is assumed that the measurement value of the SpO2 becomes abnormal (79% with respect to the normal range of 90% or higher). The control section 14 detects the abnormal state, and changes the layout so that detailed information of the vital sign which is in the abnormal state is displayed.

Figure 10B:
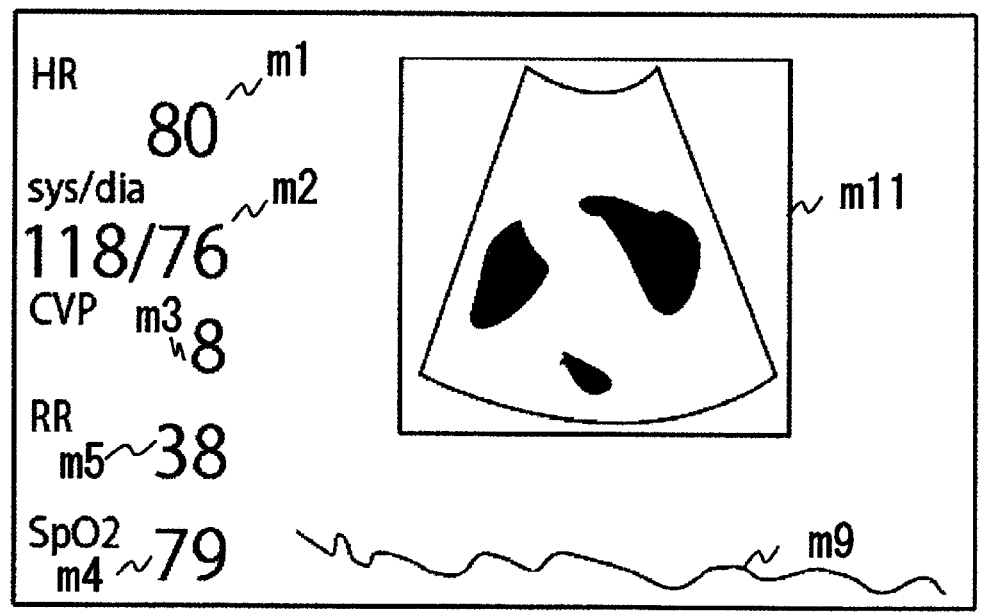
FIG. 10B is a view showing an example of a layout change in Embodiment 3.

FIG. 10B shows an example of the display screen after the layout is changed. The control section 14 changes the layout so that the display region for the ultrasonic image m11 is narrowed, and the measurement waveform m9 of the SpO2 is displayed in the space which has become vacant. This enables the user to refer the detailed information of the SpO2 which is in the abnormal state.

The layout change is a mere example. In the case where the event of (F) above occurs, the control section 14 may change the layout by using a rule equivalent to Rules 1 to 3 above.

In the above description, the control section 14 changes the layout depending on whether a certain vital sign becomes abnormal or not. In the case where a state where, although not abnormal, a vital sign is degraded for a long term (for example, the respiration rate is gradually reduced), or the like is detected, the layout may be changed. That is, the control section 14 may change the layout when a vital sign enters a predetermined degraded state.

Events functioning as a trigger for a layout change are not limited to (E) and (F) above, and the layout may be changed by using another event as a trigger.

Although, in the above-described examples (FIGS. 6A to 10B), the examples in which the control section 14 automatically changes the layout have been described, the manner of the layout change is not limited to this. In the case where a predetermined event ((E) or (F) above, or the like) in which a layout change is to be performed occurs, the control section 14 may cause a message for confirming whether a layout change is to be performed or not ("Perform a layout change"), and an operation button to be displayed on the screen, and perform a layout change in accordance with a result of inputting of the operation button.

Then, effects of the patient monitor 10 of the embodiment will be described. In the case where a predetermined event ((E) or (F) above, or the like) is detected, the patient monitor 10 of the embodiment changes the layout of a screen on which at least one of information of vital signs and an ultrasonic image is displayed (FIGS. 6A to 10B). This enables the patient monitor 10 to provide an adequate screen which corresponds to the condition of the subject, or the operation by the user.

In the case where a predetermined event ((E) or (F) above, or the like) in which a layout change is to be performed occurs, alternatively, the control section 14 may change the layout in accordance with a predetermined rule (Rules 1 to 3 above). When the rule is previously set, the patient monitor 10 can immediately cause an adequate screen to be displayed, even in an operation room or in a case of a sudden change of the subject.

In the case where Rule 1 above (the measurement values (numerical values) of vital signs are preferentially displayed) is used, for example, the patient monitor 10 can simultaneously display an ultrasonic image and measurement values of vital signs. This enables the user to refer the ultrasonic image while knowing the current condition of the subject.

In the case where Rule 2 above (the layout is changed in accordance with a preset priority order) is used, the user can refer information which the user wishes to preferentially refer, while referring an ultrasonic image.

In the case where Rule 3 above (a vital sign in an abnormal state is preferentially displayed) is used, the user can preferentially refer a vital sign which is to be referred particularly carefully, together with an ultrasonic image.

Although the invention conducted by the inventor has been specifically described based on the embodiments, the invention is not limited to the above-described embodiments, and it is a matter of course that various changes can be made without departing from the spirit of the invention.

At least a part of the processes of the above-described control section 14 may be realized as computer programs which operate in the patient monitor 10.

The programs may be stored by using a non-transitory computer readable medium of any one of various types, and then supplied to the computer. The non-transitory computer readable medium includes tangible storage media of various types. Examples of the non-transitory computer readable medium are a magnetic recording medium (for example, a flexible disk, a magnetic tape, and a hard disk drive), a magneto-optical recording medium (for example, a magneto-optical disk), a CD-ROM (Read Only Memory), a CD-R, a CD-R/W, a semiconductor memory (for example, a mask ROM, a PROM (Programmable ROM), an EPROM (Erasable PROM), a flash ROM, and a RAM (random access memory)). Alternatively, the programs may be supplied to the computer by means of a transitory computer readable medium of any one of various types. Examples of the transitory computer readable medium include an electrical signal, an optical signal, and an electromagnetic wave. The transitory computer readable medium can supply the programs to the computer through a wired communication path such as an electric wire or an optical fiber, or a wireless communication path.

That is, the control section 14 may include a processor and a memory. Examples of the processor are a CPU and an MPU. The memory is configured so as to store an instruction that is readable by a computer. Examples of the memory are a ROM which stores various instructions, and a RAM having a work area in which various instructions to be executed by the processor are stored.

As a disclosure constituting part of the disclosure of the present application, the disclosure of Japanese Patent Application No. 2015-223061 filed Nov. 13, 2015 is incorporated herein by reference.

The invention claimed is:

1. A patient monitor which acquires a plurality of vital signs that is based on physiological signals of a subject, and an ultrasonic image that is based on a received wave of an ultrasonic wave which is transmitted onto the subject, the patient monitor comprising:

a display which displays information of the subject, the information of the subject including first and second measurement values for first and second vital signs and first and second measurement waveforms for the first and the second vital signs, respectively, wherein the display is configured to operate in one from among a first mode and a second mode; and a processor configured to switch an operation mode of the display between the first mode and the second mode, wherein the first mode is for providing, on the display, a first content screen which displays the information of the plurality of vital signs, including the first and second measurement values and the first and second measurement waveforms, and which does not display the ultrasonic image, wherein the second mode is for providing, on the display, a second content screen which displays the ultrasonic image and the first measurement value, and which does not display at least a part of the second measurement waveform, wherein, in the switching between the first mode and the second mode, a position on the display of the first measurement value is not changed.

2. The patient monitor according to claim 1, wherein the processor is configured to:

in response to receiving a mode switch control signal generated in an ultrasonic measurement device and in response to a user input received through a button provided in a case of the ultrasonic measurement device used for acquiring the ultrasonic image while the display operates in the first mode, switch an operation mode of the display from the first mode to the second mode, and in response to the receiving the mode switch control signal generated in the ultrasonic measurement device and in response to a user input received through the button provided in the case of the ultrasonic measurement device while the display operates in the second mode, switch the operation mode of the display from the second mode to the first mode.

3. The patient monitor according to claim 2, wherein in a case where setting of inhibition of switching between the first mode and the second mode is made, the processor is configured to not perform switching between the first mode and the second mode.

4. The patient monitor according to claim 2, wherein, in the second mode, the processor is configured to prohibit setting related to the plurality of vital signs.

5. The patient monitor according to claim 2, wherein, in the first mode, the processor is configured to prohibit setting related to the ultrasonic image.

6. The patient monitor according to claim 2, wherein the information of the plurality of vital signs and the ultrasonic image are stored in a memory, the processor is configured to, in the first mode, read the information of the plurality of vital signs from the memory and cause the display to display the first content screen, and the processor is configured to, in the second mode, read the ultrasonic image from the memory and cause the display to display the second content screen.

7. The patient monitor according to claim 1, wherein, in response to detecting an attachment of an ultrasonic measurement device which is used for acquiring the ultrasonic image while the display operates in the first mode, the processor is configured to switch the display from the first mode to the second mode, and in response to detecting a detachment of the ultrasonic measurement device while the display operates in the second mode, the processor is configured to switch the display from the second mode to the first mode.

8. The patient monitor according to claim 1, wherein the processor is configured to:
obtain the reflection signal from an ultrasonic measurement device used for acquiring the ultrasonic image,
detect whether the reflection signal is in a state of change,
in response to the detecting that the reflection signal is in the state of change while the display operates in the first mode, switch an operation mode of the display from the first mode to the second mode, and
in response to the detecting that the reflection signal is not in the state of change for a predetermined time period while the display operates in the second mode, switch the operation mode of the display from the second mode to the first mode.

9. The patient monitor according to claim 1, wherein the processor is configured to:
determine whether the plurality of vital signs is in a degraded state,
in response to the determining that the plurality of vital signs is in the degraded state while the display operates in the second mode, switch the display from the second mode to the first mode, and
after the display is switched to operate in the first mode, determine that the plurality of vital signs is not in the degraded state for a predetermined time period, and, in response to the determining that the plurality of vital signs is not in the degraded state for the predetermined time period, switch the display from the first mode to the second mode.

10. A physiological information measurement system comprising:
the ultrasonic measurement device which receives the received wave of the ultrasonic wave which is transmitted onto the subject; and
the patient monitor according to claim 1.

11. The patient monitor according to claim 1,
wherein, in response to detection of an attachment of an ultrasonic measurement device, which is used for acquiring the ultrasonic image, while the display operates in the first mode, to the patient monitor, the processor is configured to switch the display from the first mode to the second mode.

12. The patient monitor according to claim 1, wherein the ultrasonic image is overlapped on the second measurement waveform in the second content screen.

13. The patient monitor according to claim 12, wherein the ultrasonic image is overlapped on the second measurement waveform without being overlapped on the second measurement value.

14. The patient monitor according to claim 1, wherein the first measurement waveform is displayed in both the first mode and the second mode, and in the switching between the first mode and the second mode, a position of the first measurement waveform on the display is not changed.

15. The patient monitor according to claim 1, wherein first and second measurement values are displayed in a first area of the display, and the first and second measurement waveforms are displayed in a second area of the display,
wherein the processor is further configured to:
while operating in the first mode, control the display to display, on the first content screen, the first and second measurement values in a certain order to visually correspond to the first and second measurement waveforms, and control the display to switch the operation mode from the first mode to the second mode, and
display, on the second content screen, the ultrasonic image on at least a part of the second area, and continue displaying the first and second measurement values in the certain order so that positions of the first and second measurement values on the first area of the display are not changed.

16. A patient monitor which acquires a plurality of vital signs that is based on physiological signals of a subject, and an ultrasonic image that is based on a received wave of an ultrasonic wave which is transmitted onto the subject, the patient monitor comprising:
a display which displays information of the subject, including first and second measurement values for first and second vital signs and first and second measurement waveforms for the first and the second vital signs, respectively, wherein the display is configured to operate in one from among a first mode and a second mode; and
a processor configured to switch an operation mode of the display between the first mode and the second mode,
wherein the first mode is for providing, on the display, a first content screen which displays the information of the first and second measurement values and the first and second measurement waveforms, and which does not display the ultrasonic image,
wherein the second mode is for providing, on the display, a second content screen which displays the ultrasonic image and the first measurement value and does not display the second measurement waveform,
wherein, in response to the switching from the first mode to the second mode, the processor is further configured to:
based on a first display size of the ultrasonic image, control the display to display the first and second measurement values and not to display the first and second measurement waveforms, and
based on a second display size of the ultrasonic image, control the display to display the first and second measurement values and to display the first measurement waveform, the second display size being smaller than the first display size.

\* \* \* \* \*